(12) United States Patent
Nakazawa et al.

(10) Patent No.: US 7,994,186 B2
(45) Date of Patent: Aug. 9, 2011

(54) PHARMACEUTICAL COMPOSITIONS CONTAINING CAMPTOTHECINS

(75) Inventors: Masako Nakazawa, Tokyo (JP); Ritsuo Aiyama, Tokyo (JP); Masato Nagaoka, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 219 days.

(21) Appl. No.: 11/107,881

(22) Filed: Apr. 18, 2005

(65) Prior Publication Data
US 2006/0235040 A1 Oct. 19, 2006

(51) Int. Cl.
*A01N 43/42* (2006.01)
*A61K 31/44* (2006.01)
*C07D 519/04* (2006.01)

(52) U.S. Cl. .......................... 514/283; 546/51

(58) Field of Classification Search .................. 514/283; 546/51
See application file for complete search history.

(56) References Cited

U.S. PATENT DOCUMENTS

| | | | |
|---|---|---|---|
| 4,473,692 A | 9/1984 | Miyasaka et al. | |
| 4,545,880 A | 10/1985 | Miyasaka et al. | |
| 4,604,463 A | 8/1986 | Miyasaka et al. | |
| 4,948,788 A * | 8/1990 | Makino et al. | 514/167 |
| 5,061,714 A * | 10/1991 | Tadokoro et al. | 514/309 |
| 5,122,526 A * | 6/1992 | Wall et al. | 514/253.02 |
| 5,468,754 A * | 11/1995 | Hausheer et al. | 514/283 |
| 5,942,386 A * | 8/1999 | Kmiec et al. | 435/4 |
| 6,287,602 B1 * | 9/2001 | Singh | 424/488 |
| 6,476,043 B1 * | 11/2002 | Toutain et al. | 514/280 |
| 2002/0035091 A1 * | 3/2002 | Govindarajan et al. | 514/58 |

FOREIGN PATENT DOCUMENTS

| | | |
|---|---|---|
| JP | 62-47193 | 10/1987 |
| JP | 3-4077 | 1/1991 |
| JP | 7-277981 | 10/1995 |
| JP | 10-17472 | 1/1998 |
| JP | 2003-073751 | 3/2003 |
| JP | 2004-277374 | 10/2004 |

OTHER PUBLICATIONS

Katsuya Akimoto, et al., "Kinetic Studies of the Hydrolysis and Lactonization of Camptothecin and Its Derivatives, CPT-11 and SN-38, in Aqueous Solution", Chem. Pharm. Bull. vol. 42. No. 10, Oct. 1994, pp. 2135-2138.
Katsuya Akimoto, et al., "Photodegradation reactions of CPT-II, a derivative of camptothecin. I: chemical structure of main degradation products in aqueous solution", Drug Stability, vol. 1, No. 2, 1996, pp. 118-122.
U.S. Appl. No. 10/586,879, filed Jul. 21, 2006, Nakazawa, et al.

* cited by examiner

*Primary Examiner* — Frederick Krass
*Assistant Examiner* — Benjamin Packard
(74) *Attorney, Agent, or Firm* — Oblon, Spivak, McClelland, Maier & Neustadt, L.L.P.

(57) ABSTRACT

A camptothecin-containing pharmaceutical composition which contains: (a) camptothecin or a derivative thereof, and (b) one or more compounds selected from among ascorbic acid or a salt thereof, sodium hydrogen sulfite, sodium sulfite, potassium pyrosulfite, sodium erythorbate, sodium thioglycolate, sodium pyrosulfite, and α-thioglycerin. The pharmaceutical composition is useful in that, after storage for a long period of time or under light-irradiation conditions, camptothecin or a derivative thereof contained therein undergoes minimum degradation.

22 Claims, 1 Drawing Sheet

PHARMACEUTICAL COMPOSITIONS CONTAINING CAMPTOTHECINS

BACKGROUND OF THE INVENTION

1. Field of the invention

The present invention relates to camptothecin-containing pharmaceutical compositions which, when stored for a long period of time or irradiated with light, undergo minimum degradation of camptothecin or a derivative thereof.

2. Background Art

Camptothecin (CPT) is an alkaloid contained in roots and fruit of *Camptotheca acuminata*, a deciduous tree native of China. Also, 7-ethyl-10-piperidinopiperidinocarbonyloxycamptothecin (CPT-11), which is a semi-synthetic derivative of CPT, is a particularly valuable substance for being a compound which exhibits high anti-tumor activity inherent to CPT and yet has a reduced toxicity (JP-B-1991-4077). The activity of CPT-11 is considered to be exhibited after CPT-11 is metabolized in the living body to be transformed to a semi-synthesized derivative, 7-ethyl-10-hydroxycamptothecin (SN-38) (JP-B-1987-47193).

CPT-11 is administered to a patient primarily via intravenous injection. Therefore, CPT-11 currently available on the market and distributed for use usually takes the form of an isotonic solution prepared in combination with sorbitol or physiological saline. A variety of attempts to prepare a drug product containing camptothecin have heretofore been carried out. For example, JP-A-1995-277981 discloses a sustained-release drug prepared by incorporating a camptothecin derivative into a copolymer of collagen and 2-hydroxyethylmethacrylate, and JP-A-1998-17472 discloses a sustained-release drug prepared by incorporating camptothecin or a derivative thereof into a carrier formed of a polylactic acid—glycolic acid copolymer.

Meanwhile, according to some knowledge which has heretofore been reported, a lactone-ring-open compound is formed in a CPT-11 drug, and this open-ring compound has no anti-tumor activity (Chem. Pharm. Bull. 42(10), 2135-2138 (1994)). Moreover, when irradiated with light, CPT-11 produces degradation products. Among the degradation products, D3, D2, and D3 have been reported to be three major structures (Drug Stability, Vol. 1 (2), 118 (1996)). Production of such impurities should be suppressed so as to prevent lowering of anti-tumor activity of the drug product and to avoid possible deviation from quality standards. Current camptothecin drug products are contained in light-shielding vials so as to prevent photodegradation of camptothecin. However, under typical light conditions inside a room, degradation is still observed if the drug products are stored for a long period of time. Also, in view that drug products may be placed under harsh conditions during distribution, further studies for preventing degradation are required.

Vials with light-shielding properties by nature have poor light permeability, which means that, during production steps or during storage-related quality tests, visual or mechanical inspection for any insoluble foreign matter is difficult to perform. Therefore, in the field of quality control or quality tests, use of transparent vials is keenly desired.

SUMMARY OF THE INVENTION

Under the above circumstances, the present inventors have studied in detail the mechanism by which degradation products are produced from CPT-11 drug products, and have found that after CPT-11 drug products are stored for a long period of time, a small amount of U1 (C-ring-cleaved product) is produced, and after storage under irradiation with light, many photodegradation products are produced in addition to the above-mentioned three major degradation products.

Generally, CPT-11 drug products are placed in light-shielding vials (primary package), and the vials are put in a carton box (secondary package). Under such conditions, significant effects that directly cause degradation in quality do not occur. However, it has now been clarified that, if storage conditions are deteriorated due to, for example, exposure to direct sunlight in a hospital, photodegradation products are generated, and if the storage period is long (e.g., three years), even under light-shielded conditions, CPT-11 drug products produce small amounts of U1. Therefore, in order to guarantee the quality of CPT-11 drug products, more advanced means for preventing production of degradation products is awaited.

In view of the foregoing, the present inventors have conducted extensive research, and have found that addition of a specific compound to a pharmaceutical composition containing camptothecin or a derivative thereof can effectively prevent generation of the aforementioned degradation products, thereby leading to completion of the present invention.

Accordingly, the present invention provides a camptothecin-containing pharmaceutical composition containing:

(a) camptothecin or a derivative thereof, and (b) one or more compounds selected from among ascorbic acid or a salt thereof, sodium hydrogen sulfite, sodium sulfite, potassium pyrosulfite, sodium erythorbate, sodium thioglycolate, sodium pyrosulfite, and α-thioglycerin.

Moreover, the present invention provides a method for preventing degradation of camptothecin or a derivative thereof, comprising adding, to a composition containing camptothecin or a derivative thereof, one or more compounds selected from among ascorbic acid or a salt thereof, sodium hydrogen sulfite, sodium sulfite, potassium pyrosulfite, sodium erythorbate, sodium thioglycolate, sodium pyrosulfite, and α-thioglycerin.

The pharmaceutical composition of the present invention undergoes minimum degradation of camptothecin after storage for a long period of time or storage under irradiation with light, and therefore, types of containers which have hitherto been impossible to employ—such as transparent vials, kit products which are frequently used these days, and plastic vials—an now be used, thereby not only solving quality-control-related problems but also improving, in application to kit products, handling of the products in clinical fields.

DETAILED DESCRIPTION OF PREFERRED EMBODIMENTS

Figure 1:
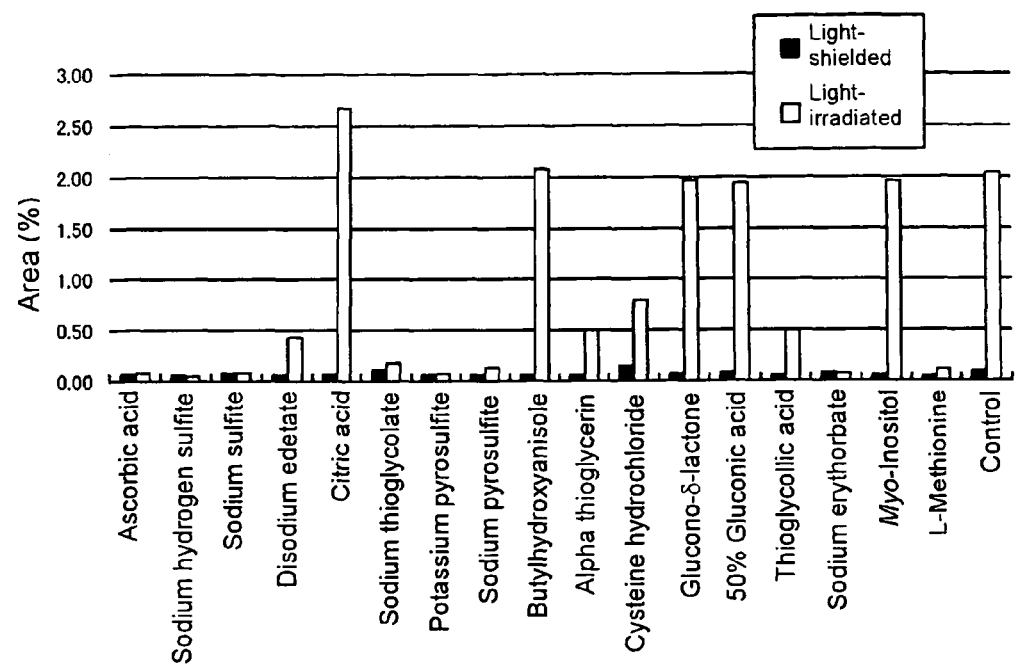
FIG. 1 is a chart showing production of U1 when a variety of additives are added to CPT-11 under light-shielded conditions or irradiation conditions.

The component (a); i.e., camptothecin or a derivative thereof (hereinafter camptothecin and derivatives thereof may be collectively called simply camptothecin), is an active ingredient of the pharmaceutical composition of the present invention. Examples of component (a) include those of natural origin, such as 10-hydroxycamptothecin, 11-hydroxycamptothecin, 9-methoxycamptothecin, 10-methoxycamptothecin, and 11-methoxycamptothecin; and camptothecin derivatives (CPT-11) which are obtained through semi-synthesis starting from any of the above-mentioned natural-origin camptothecins and subjecting the same to chemical modification.

Camptothecins; for example, CPT-11 degradation products, include, in addition to D1, D2, and D3, which are known compounds, U1, which is produced during long-term storage, and Y1, Y2, and Y3, which are produced under light irradiation conditions.

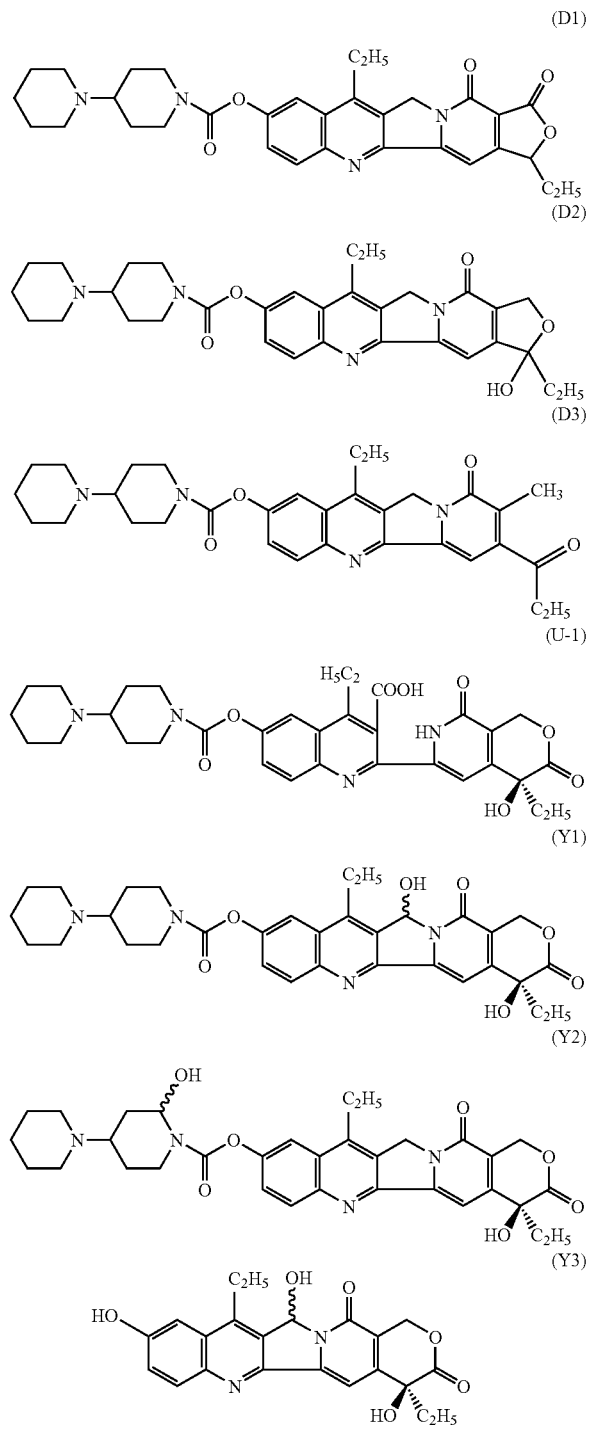

The component (b) of the pharmaceutical composition of the present invention has an effect of preventing degradation of camptothecin. Among a vast number of compounds which may serve as component (b), one or more compounds selected from among ascorbic acid or a salt thereof, sodium hydrogen sulfite, sodium sulfite, potassium pyrosulfite, sodium erythorbate, sodium thioglycolate, sodium pyrosulfite and α-thioglycerin exhibit particularly excellent degradation preventive effects. An exemplary salt of ascorbic acid is a sodium salt.

In order to ensure preventive effect against degradation of camptothecin, the component (b) is preferably contained in the pharmaceutical composition of the present invention in an amount of 1 to 300 mg, more preferably 10 to 200 mg, with respect to 100 mg of the component (a) (camptothecin).

When the pharmaceutical composition of the present invention further contain one or more organic acids selected from among acetic acid, lactic acid, succinic acid, fumaric acid, and maleic acid, formation of ring-open products of camptothecin can be significantly prevented.

No particular limitation is imposed on the amount of any of these organic acids in a pharmaceutical composition of the present invention. However, in order to ensure effective prevention against degradation of camptothecin, an amount of any of these organic acids in a pharmaceutical composition of the present invention that causes the pH of an aqueous solution of the composition containing 10 to 40 mg/mL camptothecin to fall between 2 and 5 at room temperature is preferred.

The pharmaceutical composition of the present invention is useful as an anti-tumor drug, because its active ingredient, camptothecin, has excellent therapeutic effects for malignant tumor and is stabilized for a long period of time. Examples of target malignant tumors to which the composition or the drug product of the present invention shows its efficacy include lung cancer, uterus cancer, ovarian cancer, gastric cancer, colonic/rectum cancer, breast cancer, lymphoma, and pancreatic cancer.

Preferably, the pharmaceutical composition of the present invention takes a dosage form of injection liquid, in particular that for intravenous injection. When an injection product is prepared, in addition to the above-described components, other additives may be incorporated, including: sterilized water for injection; sugars such as glucose, mannose, and lactose; inorganic salts such as common salt; organic amines such as HEPES and PIPES; and other ingredients which are ordinarily employed in preparation of injections, such as stabilizers, excipients, and buffers. In an injection product, camptothecin is preferably contained in 1 to 50 mg/mL, more preferably 10 to 30 mg/mL.

EXAMPLES

The present invention will next be described in more detail by way of examples, which should not be construed as limiting the invention thereto. In an extension study, U1, which is formed after storage for a long period of time, was found to be degraded in a shorter period of time under irradiation with light, and therefore, assessment in relation to U1 was performed by short-term testing on the basis of photodegradation.

Example 1

(1) 0.5 wt. % Acetic acid (pH 3.1; 250 mL) was added to about 5g of CPT-11, and the mixture (20 mg/mL) was dissolved in an oil bath of about 80° C. After having been left to cool, the solution was filtered through a 0.22 μm membrane filter. An additive was added to the resultant solution. After complete dissolution, the solution was divided into two aliquots, and each of them was individually placed in a transparent glass vial provided with a lid. One was light-shielded and put in a photostability testing apparatus. The other was put in the same testing apparatus but without light-shielding. The solutions were irradiated with light of 1.2 million Lx/hr at 25° C. The solutions were analyzed by HPLC, and levels of degradation products produced in a light-shielded sample and a light-irradiated sample were compared.

HPLC conditions

Column: Cadenza CD-C18 4.6×150 mm

Mobile phase: MeCN/50 mM formate buffer (pH: about 5.1)/MeOH =10/75/15→30/55/15, linear gradient, 30 minutes Column temperature: 50° C.

Flow: 1.5 mL/min

Injection volume: 0.2 μL

Detection wavelength: 254 nm

Each additive, in an appropriate amount, was added to a CPT-11 drug product (CPT-11: 100 mg/5 mL), to prepare a test sample. All the additives selected have a history of being used as additives in drug products for human use. The relations between the additives and the amounts of addition are shown in Table 1.

TABLE 1

| No. | Additive | Experience of use in IV | Amount added (mg/5 mL) | Max amount of use in IV (per day) |
|---|---|---|---|---|
| 1 | Ascorbic acid | yes | 200*[1] | 2.8 g |
| 2 | Sodium hydrogen sulfite | yes | 200*[1] | 800 mg |
| 3 | Sodium sulfite | yes | 60 | 60 mg |
| 4 | Disodium edetate | yes | 29 | 29 mg |
| 5 | Citric acid | yes | 184 | 184 mg |
| 6 | Sodium thioglycolate | yes | 20 | 20 mg |
| 7 | Potassium pyrosulfite | yes | 200*[1] | 1250 mg |
| 8 | Sodium pyrosulfite | yes | 40 | 40 mg |
| 9 | Butylhydroxyanisole | yes | 0.075 | 75 μg |

TABLE 1-continued

| No. | Additive | Experience of use in IV | Amount added (mg/5 mL) | Max amount of use in IV (per day) |
|---|---|---|---|---|
| 10 | L-Arginine | yes | 200*[1] | 457.5 mg |
| 11 | Alpha thioglycerin | yes | 24 | 24 mg |
| 12 | Cysteine hydrochloride | yes | 16 | 16.8 mg |
| 13 | Anhydrous sodium sulfite | yes | 200*[1] | 1 g |
| 14 | Glucono-δ-lactone | no | 50*[2] | — |
| 15 | 50% Gluconic acid | no | 100*[2] | — |
| 16 | Thioglycollic acid | yes | 2.5 | 2.5 mg |
| 17 | Sodium thiosulfate | yes | 3 | 3 mg |
| 18 | Sodium erythorbate | no | 50*[2] | — |
| 19 | Myo-Inositol | yes | 50 | 50 mg |
| 20 | L-Methionine | no | 50*[2] | — |
| 21 | tris(Hydroxymethyl)-aminomethane | yes | 72 | 72 mg |

*[1]For those that have heretofore been used in intravenous injection (IV) at a max amount of 200 mg or more, the amount of addition was uniformly set at 200 mg.
*[2]Those that have not been used in intravenous injection (IV) were added in amounts of 50 mg per 5 mL. However, 50% gluconic acid was added in an amount of 100 mg per 5 mL for having a concentration of 50%.
Other additives were added in their maximum amounts.

FIG. 1 shows production of U1 in CPT-11 drug products to which respective additives were individually incorporated. As is apparent from FIG. 1, five additives; i.e., ascorbic acid, sodium hydrogen sulfite, sodium sulfite, potassium pyrosulfite, and sodium erythorbate, prevent production of U1.

(2) Table 2 shows percentages of "photodegradation product produced in light-irradiation sample" and "photodegradation product produced in light-shielded sample," wherein the photodegradation products investigated are typical photodegradation products; i.e., Y1, Y2, Y3, D1, D2, and D3. Table 2 also shows percentages of residual CPT-11 in light-irradiated samples and light-shielded samples. In light-irradiated samples, many unidentifiable peaks are observed, but 6 additives; i.e., ascorbic acid, sodium hydrogen sulfite, sodium thioglycolate, potassium pyrosulfite, sodium pyrosulfite, and alpha-thioglycerin, were found to prevent generation of degradation products caused by irradiation with light.

TABLE 2

| Additive | Condition | U1 | Y1 | Y2 | Y3 | CPT-11 | D2 | D1 | D3 |
|---|---|---|---|---|---|---|---|---|---|
| 1 Ascorbic acid | Shield | 0.07 | 0.05 | 0.20 | 0.08 | 99.47 | UD | UD | UD |
| | Irrad. | 0.08 | 0.06 | 0.46 | 0.17 | 98.40 | UD | UD | UD |
| 2 Sodium hydrogen sulfite | Shield | 0.06 | UD | 0.16 | UD | 99.59 | UD | UD | UD |
| | Irrad. | 0.05 | UD | 0.25 | 0.08 | 97.99 | UD | 0.11 | UD |
| 3 Sodium sulfite | Shield | 0.08 | UD | 0.43 | UD | 97.86 | 0.31 | 0.22 | UD |
| | Irrad. | 0.08 | UD | 0.19 | 3.52 | 74.11 | 8.94 | 0.30 | 8.34 |
| 4 Disodium edetate | Shield | 0.06 | UD | UD | UD | 99.89 | UD | UD | UD |
| | Irrad. | 0.43 | 0.12 | 0.99 | 0.84 | 84.36 | 2.79 | UD | 6.57 |
| 5 Citric acid | Shield | 0.07 | UD | UD | UD | 99.93 | UD | UD | UD |
| | Irrad. | 2.67 | UD | 3.70 | 0.28 | 82.49 | UD | 7.12 | UD |
| 6 Sodium thioglycolate | Shield | 0.11 | 0.29 | 0.74 | 0.19 | 97.84 | UD | 0.20 | UD |
| | Irrad. | 0.18 | 0.13 | 0.70 | 0.50 | 92.52 | 1.39 | 1.60 | 1.74 |
| 7 Potassium pyrosulfite | Shield | 0.06 | UD | 0.15 | UD | 99.62 | UD | UD | UD |
| | Irrad. | 0.07 | UD | 0.20 | 0.09 | 98.03 | UD | 0.12 | UD |
| 8 Sodium pyrosulfite | Shield | 0.06 | UD | 0.52 | UD | 99.18 | UD | 0.12 | UD |
| | Irrad. | 0.13 | UD | 0.83 | 0.13 | 95.99 | UD | 0.38 | UD |
| 9 Butylhydroxyanisole | Shield | 0.06 | UD | UD | UD | 99.94 | UD | UD | UD |
| | Irrad. | 2.08 | UD | 3.02 | 0.57 | 82.66 | 0.46 | 7.39 | UD |
| 10 L-Arginine | Test was stopped because of additive's insolubility | | | | | | | | |
| 11 Alpha thioglycerin | Shield | 0.06 | UD | 0.27 | UD | 99.42 | UD | 0.09 | UD |
| | Irrad. | 0.50 | UD | 1.94 | 0.16 | 91.71 | UD | 3.53 | 0.24 |
| 12 Cysteine hydrochloride | Shield | 0.15 | UD | 0.41 | 0.08 | 98.98 | UD | 0.24 | UD |
| | Irrad. | 0.79 | UD | 2.70 | 0.31 | 88.65 | 0.11 | 4.93 | UD |
| 13 Anhydrous sodium sulfite | Test was stopped because precipitation settled after irradiation with light | | | | | | | | |
| 14 Glucono-δ-lactone | Shield | 0.07 | UD | UD | UD | 99.93 | UD | UD | UD |
| | Irrad. | 1.97 | UD | 3.11 | 0.42 | 83.10 | 0.28 | 7.61 | UD |

TABLE 2-continued

| | | | | | | | (Area: %) | | |
|---|Additive|Condition|U1|Y1|Y2|Y3|CPT-11|D2|D1|D3|
|---|---|---|---|---|---|---|---|---|---|---|
|15|50% Gluconic acid|Shield|0.08|UD|UD|UD|99.92|UD|UD|UD|
| | |Irrad.|1.94|UD|3.10|0.43|83.20|0.29|7.47|0.10|
|16|Thioglycollic acid|Shield|0.06|UD|0.22|UD|99.60|UD|UD|UD|
| | |Irrad.|0.50|UD|2.23|0.18|89.06|0.07|4.49|0.16|
|17|Sodium thiosulfate|colspan: Test was stopped because precipitation settled after irradiation with light|
|18|Sodium erythorbate|Shield|0.08|UD|0.78|0.23|97.39|UD|0.14|UD|
| | |Irrad.|0.07|UD|0.66|0.64|92.45|1.85|0.34|1.69|
|19|Myo-Inositol|Shield|0.06|UD|UD|UD|99.94|UD|UD|UD|
| | |Irrad.|1.96|UD|2.83|0.56|82.93|0.53|7.72|0.14|
|20|L-Methionine|Shield|0.05|0.11|UD|UD|99.90|UD|UD|UD|
| | |Irrad.|0.11|UD|0.35|0.22|91.16|0.66|0.08|5.34|
|21|tris(Hydroxymethyl)-aminomethane|colspan: Test was stopped because of formation of turbidity|
| |Control|Shield|0.09|UD|UD|UD|99.84|UD|0.06|UD|
| | |Irrad.|2.04|UD|2.95|0.56|82.96|0.50|7.27|0.13|

Shield: Light-shielded
Irrad.: Irradiated with light
UD: Undetected

Data of respective degradation products obtained from different analytical devices are shown below.

D1
 MS(APCI):m/z 557 [M+H]$^+$($C_{32}H_{36}N_4O_5$:556)
 IR(KBr) $v cm^{-1}$:2960,1764,1660,1598.
 $^1$H-NMR(CDCl$_3$)δ: 1.06(3H,t,J=7 Hz),1.42(3H,t,J=8 Hz), 1.93, 2.23(2H,m),3.18(2H,q,J=8 Hz),5.33(2H,s),5.40(1H,t,J=5 Hz), 7.30(1H,s),7.61(1H,dd,J=9 & 2 Hz),7.89(1H,d,J=2 Hz), 8.23(1H,d,J=9 Hz)

D2
 MS (APCI):m/z 559 [M+H]$^+$($C_{32}H_{38}N_4O_5$:558)
 IR(KBr)$v cm^{-1}$:2946, 1725,1670,1593,1070.
 $^1$H-NMR(CDCl$_3$)δ:1.04(3H,t,J=7 Hz),1.24(3H,t,J=8 Hz), 2.26(2H,q,J=8 Hz),2.95(2H,m),5.07(1H,d,J=17 Hz), 5.21 (1H,d,J=17 Hz),7.25(1H,s),7.43(1H,d,J=9 Hz), 7.65(1H,s), 7.88(1H,d,J=9 Hz).

D3
 MS(APCI):m/z 543 [M+H]$^+$($C_{32}H_{38}N_4O_4$:542)
 IR(KBr)$v cm^{-1}$:2942,1715,1656,1608.
 $^1$H-NMR(CDCl$_3$)δ:1.24(3H,t,J=7 Hz),1.41(3H,t,J=8 Hz), 2.30(3H,s),2.81(2H,q,J=7 Hz),3.18(2H,q,J=8 Hz), 5.26(2H,s),7.21(1H,s),7.56(1H,dd,J=9 Hz & 2 Hz), 7.81(1H,d,J=2 Hz),8.18(1H,d,J=9 Hz).

Y1
 MS(APCI):m/z 603 [M+H]$^+$($C_{33}H_{38}N_4O_7$:602)
 $^1$H-NMR(CDCl$_3$)δ:1.01 & 1.03(3H×2,t×2,J=7 Hz), 1.44 (3H×2,t×2,J=7 Hz),1.85(2H×2,q×2,J=7 Hz), 3.21 & 3.55 (4H,m),4.35 & 4.41(2H×2,br d×2), 5.24 & 5.25(1H×2,d×2, J=16 Hz),5.66 & 5.67(1H×2,d×2,J=16 Hz), 7.08 & 7.10(1H×2,s×2),7.51 & 7.54(1H×2,s×2), 7.54 & 7.56(1H×2,dd×2, J=10 Hz & 3 Hz), 7.82 & 7.83(1H×2,d×2,J=3 Hz),8.13 & 8.16(1H×2,d×2,J=10 Hz).

Y2
 MS(SIMS):m/z 603 [M+H]$^+$($C_{33}H_{38}N_4O_7$:602)
 IR(KBr)$v cm^{-1}$:2940, 1715,1660,1600,1180.
 $^{13}$C-NMR(CDCl$_3$)δ:173.6(2),157.4(17),151.2(23),150.4 (7), 150.0(4,11),146.8(6,8),145.0(14),131.5(9),127.0(13,15), 125.3(10),118.5(18),114.2(12),97.9(5),75.5(24),72.8(3), 66.1(1), 56.1(26),50.1(16),49.3(29,33),36.9(28),31.9(19), 29.7(25,27),27.6(25,27),26.0(30,32),24.5(21),23.0(31), 13.9 (22),7.8(20)

Y3
 $^1$H-NMR(CDCl$_3$)δ:1.04 & 1.05(3H×2,t×2,J=7 Hz), 1.43 & 1.44(3H×2,t×2,J=7 Hz),1.88(2H×2,q×2,J=7 Hz), 3.18 & 3.32(4H,m),5.26 & 5.27(1H×2,d×2,J=17 Hz), 5.08 & 5.70(1H×2,d×2,J=17 Hz),7.04 & 7.08(1H×2,br s), 7.42 & 7.43(1H×2,s×2),7.52 & 7.53(1H×2,br×2), 7.69(1H×2,br d),8.12(1H×2,br d,J=10 Hz).

U1
 MS(APCI):m/z 619 [M+H]$^+$($C_{33}H_{38}N_4O_8$:618)
 $^1$H-NMR(DMSO)δ:0.91(3H,t,J=8 Hz),1.24(3H,t,J=8 Hz), 1.5-2.2(9H,m),2.09(2H,br.d),3.13(2H,m),3.41(2H,m),3.51 (2H,m), 3.61(2H,m),3.85(1H,br),3.90(1H,br.d),4.51(1H, br.d), 5.33(2H,s),6.20(2H,s),7.18(2H,s),7.70(1H,dd,J=9 Hz,2 Hz), 7.95(1H,d,J=2 Hz),8.41(1H,d,J=9 Hz).

Example 3

The injection products of Product Examples 1 to 3 described below were prepared through the following production process.

Irinotecan hydrochloride (100 mg) was added to water for injection (4.5 mL), and the mixture was heated at 90° C. for dissolution. The additives were added, dissolved, and then a suitable amount of sodium hydroxide was added, so as to adjust pH to about 4. Water for injection was added to make the total volume 5 mL.

Product Example 1

| | |
|---|---|
| Irinotecan hydrochloride | 100 mg |
| D-Glucose | 225 mg |
| Ascorbic acid | 200 mg |
| Sodium hydroxide | Suitable amount |
| Water for injection | to make the volume 5 mL |

Product Example 2

| | |
|---|---|
| Irinotecan hydrochloride | 100 mg |
| D-Glucose | 225 mg |
| Sodium pyrosulfite | 40 mg |
| Lactic acid | 4.5 mg |
| Sodium hydroxide | Suitable amount |
| Water for injection | to make the volume 5 mL |

Product Example 3

| | |
|---|---|
| Irinotecan hydrochloride | 100 mg |
| D-Glucose | 225 mg |
| Alpha-Thioglycerin | 24 mg |
| Lactic acid | 4.5 mg |
| Sodium hydroxide | Suitable amount |
| Water for injection | to make the volume 5 mL |

What is claimed is:

1. A camptothecin-containing pharmaceutical composition comprising:
   (a) 10 to 40 mg/mL of a camptothecin selected from the group consisting of camptothecin, 10-hydroxycamptothecin, 11-hydroxycamptothecin, 9-methoxycamptothecin, 10-methoxycamptothecin, 11-methoxycamptothecin, and 7-ethyl-10-piperidinopiperidinocarbonyloxycamptothecin, and
   (b) 1 to 300 mg per 100 mg of component (a) of one or more compounds selected from the group consisting of potassium pyrosulfite, sodium erythorbate, sodium thioglycolate, sodium pyrosulfite, and α-thioglycerin.

2. The camptothecin-containing pharmaceutical composition according to claim 1, further comprising: one or more organic acids selected from the group consisting of acetic acid, lactic acid, succinic acid, fumaric acid, and maleic acid.

3. The camptothecin-containing pharmaceutical composition according to claim 1, wherein the pH of an aqueous solution comprising camptothecin in an amount of 10 to 40 mg/mL is 2 to 5.

4. The camptothecin-containing pharmaceutical composition according to claim 2, wherein the pH of an aqueous solution comprising camptothecin in an amount of 10 to 40 mg/mL is 2 to 5.

5. The camptothecin-containing pharmaceutical composition according to claim 1, which is a composition in injectable form.

6. The camptothecin-containing pharmaceutical composition according to claim 2, which is a composition in injectable form.

7. The camptothecin-containing pharmaceutical composition according to claim 3, which is a composition in injectable form.

8. The camptothecin-containing pharmaceutical composition according to claim 4, which is a composition in injectable form.

9. A method for minimizing degradation of a camptothecin, comprising adding, to a composition containing 10 to 40 mg/mL of said camptothecin, 1 to 300 mg per 100 mg of said camptothecin of one or more compounds selected from the group consisting of potassium pyrosulfite, sodium erythorbate, sodium thioglycolate, sodium pyrosulfite, and α-thioglycerin, wherein said camptothecin is selected from the group consisting of camptothecin, 10-hydroxycamptothecin, 11-hydroxycamptothecin, 9-methoxycamptothecin, 10-methoxycamptothecin, 11-methoxycamptothecin, and 7-ethyl-10-piperidinopiperidinocarbonyloxycamptothecin.

10. The method for minimizing degradation of a camptothecin according to claim 9, further comprising adding, to said composition containing said camptothecin, one or more compound selected from the group consisting of ascorbic acid, a salt of ascorbic acid, sodium sulfite, and sodium hydrogen sulfite.

11. The camptothecin-containing pharmaceutical composition according to claim 1, further comprising one or more compound selected from the group consisting of ascorbic acid, a salt of ascorbic acid, sodium sulfite, and sodium hydrogen sulfite.

12. A camptothecin-containing pharmaceutical composition comprising:
   (a) 10 to 40 mg/mL of a camptothecin selected from the group consisting of 11-methoxycamptothecin and 7-ethyl-10-piperidinopiperidinocarbonyloxycamptothecin, and
   (b) 1 to 300 mg per 100 mg of component (a) of one or more compounds selected from the group consisting of sodium hydrogen sulfite, potassium pyrosulfite, sodium erythorbate, sodium thioglycolate, sodium pyrosulfite, and α-thioglycerin.

13. The camptothecin-containing pharmaceutical composition according to claim 12, further comprising: one or more organic acids selected from the group consisting of acetic acid, lactic acid, succinic acid, fumaric acid, and maleic acid.

14. The camptothecin-containing pharmaceutical composition according to claim 12, wherein the pH of an aqueous solution comprising camptothecin in an amount of 10 to 40 mg/mL is 2 to 5.

15. The camptothecin-containing pharmaceutical composition according to claim 13, wherein the pH of an aqueous solution comprising camptothecin in an amount of 10 to 40 mg/mL is 2 to 5.

16. The camptothecin-containing pharmaceutical composition according to claim 12, which is a composition in injectable form.

17. The camptothecin-containing pharmaceutical composition according to claim 13, which is a composition in injectable form.

18. The camptothecin-containing pharmaceutical composition according to claim 14, which is a composition in injectable form.

19. The camptothecin-containing pharmaceutical composition according to claim 15, which is a composition in injectable form.

20. A method for minimizing degradation of a camptothecin, comprising adding, to a composition containing 10 to 40 mg/mL of said camptothecin, 1 to 300 mg per 100 mg of said camptothecin of one or more compounds selected from the group consisting of sodium hydrogen sulfite, potassium pyrosulfite, sodium erythorbate, sodium thioglycolate, sodium pyrosulfite, and α-thioglycerin, wherein said camptothecin is selected from the group consisting of 11-methoxycamptothecin and 7-ethyl-10-piperidinopiperidinocarbonyloxycamptothecin.

21. The camptothecin-containing pharmaceutical composition according to claim 12, further comprising ascorbic acid or a salt thereof.

22. The method for preventing degradation of a camptothecin according to claim 20, further comprising adding, to said composition containing said camptothecin, ascorbic acid or a salt thereof.

* * * * *